United States Patent [19]

Gatzke

[11] Patent Number: 5,158,087
[45] Date of Patent: Oct. 27, 1992

[54] DIFFERENTIAL TEMPERATURE MEASUREMENT FOR ULTRASOUND TRANSDUCER THERMAL CONTROL

[75] Inventor: Ronald D. Gatzke, Lexington, Mass.

[73] Assignee: Hewlett-Packard Company, Palo Alto, Calif.

[21] Appl. No.: 830,015

[22] Filed: Jan. 31, 1992

[51] Int. Cl.$^5$ ................................................ A61B 8/00
[52] U.S. Cl. .......................... 128/662.03; 128/660.06; 128/660.02; 128/736
[58] Field of Search ....................... 128/660.02, 660.06, 128/662.03, 736

[56] References Cited

U.S. PATENT DOCUMENTS

| | | | |
|---|---|---|---|
| 3,901,242 | 8/1975 | Storz | 128/303.15 |
| 4,116,198 | 9/1978 | Roos | 128/303.15 |
| 4,441,486 | 4/1984 | Pounds | 128/24A |
| 4,620,546 | 11/1986 | Aida et al. | 128/660 |
| 4,681,122 | 7/1987 | Winters et al. | 128/736 |
| 4,716,897 | 1/1988 | Noguchi et al. | 128/303.15 |
| 4,817,615 | 4/1989 | Fukukita et al. | 128/660.02 |
| 4,901,734 | 2/1990 | Griffin et al. | 128/692 |
| 4,920,978 | 5/1990 | Colvin | 128/784 |
| 4,960,109 | 10/1990 | Lele | 128/736 |
| 4,977,902 | 12/1990 | Sekino et al. | 128/804 |
| 5,015,102 | 5/1991 | Yamaguchi | 374/107 |
| 5,018,872 | 5/1991 | Suszynski et al. | 374/133 |
| 5,029,582 | 7/1991 | Lekholm | 128/736 |

*Primary Examiner*—William E. Kamm
*Assistant Examiner*—George Manuel

[57] ABSTRACT

The surface temperature of tissue adjacent to an ultrasound transducer in an ultrasound imaging probe is determined by a differential measurement technique. A first temperature representative of the temperature of the ultrasound transducer is measured with a first temperature sensor. A second temperature representative of the ambient temperature of the tissue in a region that is thermally isolated from the ultrasound transducer is measured with a second temperature sensor. The surface temperature of the tissue adjacent to the ultrasound transducer is calculated from the first measured temperature and the second measured temperature. The energy transmitted by the ultrasound transducer can be controlled in response to the calculated surface temperature, typically by reducing the transmitted ultrasound energy when the calculated surface temperature exceeds a temperature limit.

18 Claims, 1 Drawing Sheet

DIFFERENTIAL TEMPERATURE MEASUREMENT FOR ULTRASOUND TRANSDUCER THERMAL CONTROL

FIELD OF THE INVENTION

This invention relates to methods and apparatus for measuring the surface temperature of biological tissue adjacent to a transducer and, more particularly, to a technique which permits accurate measurement of surface temperature without perturbing the pattern of radiation transmitted by the transducer.

BACKGROUND OF THE INVENTION

Ultrasound imaging systems for medical diagnosis are well known. In general, an ultrasound transducer transmits ultrasound energy into a region of interest in a patient's body. The ultrasound energy is reflected by different organs and different tissue types. The reflected energy is sensed by the transducer, and the resulting electrical signal is processed to provide an image of the region of interest.

Ultrasound imaging can be performed with transducers located externally or internally. To perform internal imaging, an ultrasound transducer is mounted near the distal end of a probe that is sized and shaped for insertion within a body cavity or passage. For example, ultrasound imaging probes have been developed for use in the esophagus. An example of such a probe is a Model 21362, manufactured and sold by Hewlett Packard Company.

Although the power level transmitted by typical ultrasound imaging transducers is on the order of about 0.1 watt, some heating of the tissue adjacent to the transducer occurs. The maximum heating typically occurs at the surface of the tissue directly adjacent to the ultrasound transducer. The surface temperature of the tissue should not exceed about 41° C., or about 4° C. above normal body temperature, to prevent thermal damage to the tissue. It is thus desirable to monitor the surface temperature of the tissue adjacent to the ultrasound transducer during the imaging procedure. If the maximum allowable temperature is exceeded, the transmitted power can be reduced or turned off entirely.

Although the most straightforward approach to temperature measurement is to place a temperature sensor directly at the tissue surface where maximum heating occurs, this technique has the disadvantage that the temperature sensor causes a perturbation in the transmitted and received ultrasound patterns, and thus reduces the accuracy of the image obtained.

In present practice, a single temperature measurement is taken at a point in thermal proximity to the tissue surface of maximum heating but spaced from that surface. The single temperature measurement contains both surface and ambient temperature information in a relationship that depends upon the geometry of the energy emitting element, the transducer housing and the temperature sensor. The ambient temperature is defined as the patient's body temperature in the region of the probe but thermally isolated from the transducer. Since it is impossible to determine both the ambient and surface temperatures from a single temperature measurement, the reading is typically calibrated for a normal ambient body temperature of 37° C. While this technique provides reasonably accurate measurements of surface temperature when the actual ambient temperature is the same as the calibration value, large errors can occur when the ambient body temperature differs from the calibration value, such as may occur during cardiac surgery.

As an example of this problem, consider a transducer calibrated at a normal body temperature of 37° C. and energized to produce a tissue surface temperature of 41° C. The single temperature sensor may measure a temperature of 39° C. When the transducer is placed in a patient whose body temperature is 37° C., the measured temperature will be 39° C. and an equation used for calculating tissue surface temperature will accurately predict the tissue surface temperature of 41° C. When the patient's temperature is reduced to 25° C., a common value during cardiac surgery, and the temperature sensor reads 39° C., the actual tissue surface temperature will be 49° C. The prediction equation predicts a surface temperature of 41° C., since it assumes an ambient temperature of 37° C. Thus, there is an error of 8° C. in the predicted tissue surface temperature.

Probes and catheters having temperature sensors are disclosed in U.S. Pat. No. 4,960,109 issued Oct. 2, 1990 to Lele, U.S. Pat. No. 4,681,122 issued Jul. 21, 1987 to Winters et al and U.S. Pat. No. 4,901,737 issued Feb. 20, 1990 to Griffin et al. None of these patents disclose a technique for measuring the surface temperature of tissue adjacent to a transducer.

It is a general object of the present invention to provide improved methods and apparatus for measurement of tissue surface temperature during application of energy to biological tissue.

It is another object of the present invention to provide improved methods and apparatus for measurement of tissue surface temperature during ultrasound imaging.

It is a further object of the present invention to provide methods and apparatus for differential temperature measurement of tissue surface temperature during ultrasound imaging without perturbing the ultrasound image.

It is yet another object of the present invention to provide methods and apparatus for accurate measurement of tissue surface temperature during ultrasound imaging.

It is another object of the present invention to provide methods and apparatus for accurate control of maximum tissue surface temperature during ultrasound imaging.

SUMMARY OF THE INVENTION

According to the present invention, these and other objects and advantages are achieved in methods and apparatus for determining the surface temperature of tissue adjacent to a transducer that applies energy to the tissue. A method in accordance with the invention comprises the steps of measuring a first temperature representative of the temperature of the transducer, measuring a second temperature representative of the ambient temperature of the tissue in a region that is thermally isolated from the transducer, and calculating the surface temperature of the tissue adjacent to the transducer from the first measured temperature and the second measured temperature.

The transducer typically comprises an ultrasound transducer mounted in a probe. The first temperature is typically measured with a first temperature sensor in thermal proximity to the ultrasound transducer. The second temperature is typically measured with a second temperature sensor attached to the probe and thermally isolated from the ultrasound transducer. The surface temperature is calculated in accordance with:

$$T_{surf} = (1 - 1/k)T_2 + (1/k)T_1$$

where:
$T_{surf}$ = surface temperature;
$T_1$ = first temperature;
$T_2$ = second temperature; and
$k$ = a constant.

According to a further aspect of the invention, the power applied to the transducer is controlled in response to the calculated surface temperature. In a preferred embodiment, the power is controlled such that the ultrasound energy transmitted by the ultrasound transducer is reduced when the calculated surface temperature exceeds a temperature limit.

According to another aspect of the invention, there is provided apparatus for application of ultrasound energy to biological tissue. The apparatus comprises a probe having an ultrasound transducer mounted therein, a first temperature sensor mounted in the probe for sensing a first temperature representative of the temperature of the emitting face of the ultrasound transducer, a second temperature sensor mounted in the probe for sensing a second temperature representative of the ambient temperature of the biological tissue in the region of the probe, a power source for energizing the ultrasound transducer, and means for calculating the surface temperature of the tissue adjacent to the ultrasound transducer from the first sensed temperature and the second sensed temperature.

BRIEF DESCRIPTION OF THE DRAWINGS

For a better understanding of the present invention, together with other and further objects, advantages, and capabilities thereof, reference is made to the accompanying drawings which are incorporated herein by reference and in which.

DETAILED DESCRIPTION OF THE INVENTION

Figure 1:
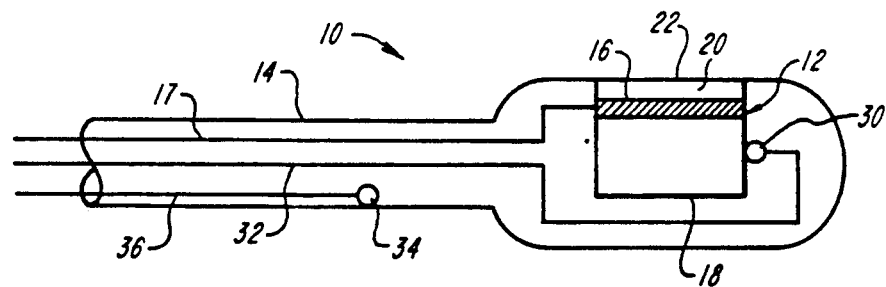
FIG. 1 is a simplified schematic diagram of an ultrasound imaging probe incorporating differential temperature measurement in accordance with the present invention.

An ultrasound imaging probe 10 is shown schematically in FIG. 1. An ultrasound transducer 12 is mounted in an elongated probe shaft 14. The probe shaft 14 is fabricated of a biologically compatible material such as polyvinylchloride and is dimensioned for insertion within a body cavity or passage, such as the esophagus. The ultrasound transducer 12 includes a piezoelectric crystal 16 mounted on a backing material 18. An ultrasound lens 20 fabricated of an electrically insulating material is mounted between the piezoelectric crystal 16 and the external surface of probe shaft 14. The piezoelectric crystal 16 is connected by electrical leads 17 through probe shaft 14 to an external power source (not shown in FIG. 1). The ultrasound transducer 12 transmits ultrasound energy through a surface 22 of probe 10 into the adjacent tissue. The surface 22 is typically in contact with tissue during operation. The structural details of the probe are known to those skilled in the art and are outside the scope of the present invention. An example of an ultrasound imaging probe is a Model 21362, manufactured and sold by Hewlett Packard Company.

In accordance with the present invention, the probe 10 is provided with temperature sensors which permit accurate determination of the surface temperature of the tissue at surface 22 adjacent to ultrasound transducer 12. A first temperature sensor 30 is positioned in probe 10 for measurement of a temperature that is proportional to the temperature of the emitting face of ultrasound transducer 12. The temperature sensor 30 is mounted so as to be in thermal proximity to piezoelectric crystal 16. Typically, the backing material 18 is thermally conductive, and the temperature sensor 30 is advantageously attached to backing material 18 as close as possible to piezoelectric crystal 16. The temperature sensor 30 is connected by electrical leads 32 through probe shaft 14 to external processing circuitry, as described below.

A second temperature sensor 34 is mounted in probe shaft 14 for measurement of the ambient body temperature of the patient. The temperature sensor 34 is connected by electrical leads 36 through probe shaft 14 to the external processing circuitry. The temperature sensor 34 is positioned on probe shaft 14 to measure the ambient tissue temperature. The temperature sensor 34 is spaced sufficiently from ultrasound transducer 12 to avoid heating effects from the transmitted ultrasound energy. Typically, a spacing of about one inch or more from ultrasound transducer 12 is sufficient to thermally isolate temperature sensor 34 from transducer 12. The temperature sensor 34 is preferably positioned sufficiently close to ultrasound transducer 12 to measure the ambient temperature close to the region to which ultrasound energy is being applied. This is particularly important where the body temperature of the patient may be locally reduced during surgery. The temperature sensors 30 and 34 preferably comprise thermistors attached to the desired element with a thermally conductive adhesive. Alternatively, thermocouples or other suitable temperature sensors can be utilized.

Figure 2:
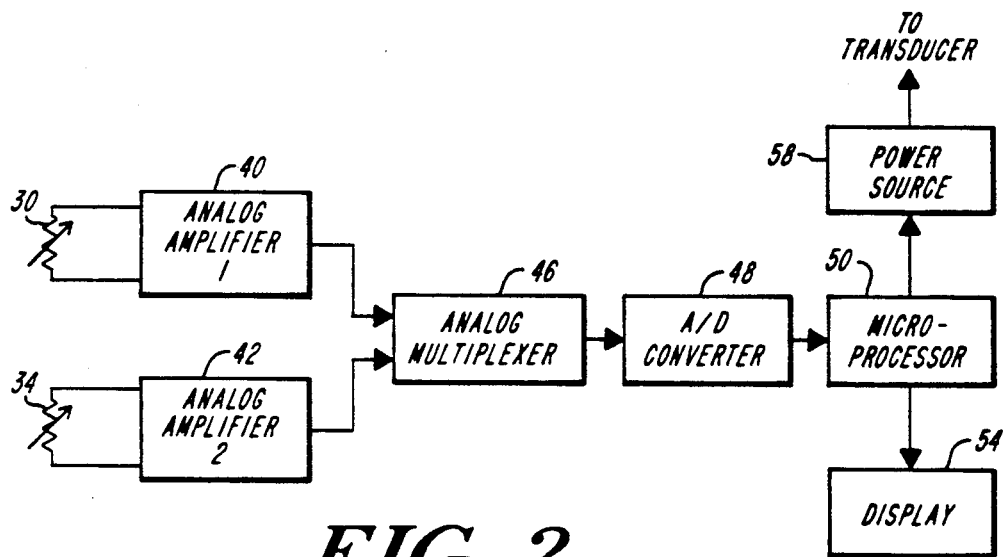
FIG. 2 is a block diagram of a system for processing the outputs of the temperature sensors.

A block diagram of one example of suitable processing circuitry is shown in FIG. 2. Temperature sensor 30 is connected to the input of an analog amplifier 40, and temperature sensor 34 is connected to the input of an analog amplifier 42. In the embodiment of FIG. 2, the temperature sensors 30 and 34 are thermistors which have a resistance that varies with temperature. The analog amplifiers 40 and 42 can be conventional differential amplifier circuits for use with thermistors. The outputs of analog amplifiers 40 and 42 are sequentially connected by an analog multiplexer 46 to the input of an analog to digital converter 48. The outputs of amplifiers 40 and 42 are voltages which represent the respective sensed temperatures. The digitized amplifier output voltages are supplied by analog-to digital converter 48 to a microprocessor 50. The microprocessor 50 calculates the temperature of the tissue at surface 22 as described below. In a preferred embodiment, microprocessor is a type 68000. However, it will be understood that any suitable microprocessor or general purpose digital or analog computer can be used to calculate the surface temperature.

The microprocessor 50 sequentially receives and stores digital representations of the temperatures sensed by sensors 30 and 34. The surface temperature at surface 22 is calculated in accordance with the following equation:

$$T_{surf} = (1 - 1/k)T_2 + (1/k)T_1 \quad (1)$$

where:
- $T_{surf}$ = tissue surface temperature;
- $T_1$ = temperature sensed by sensor (proportional to transducer temperature);
- $T_2$ = temperature sensed by sensor 34 (ambient temperature); and
- k = a constant that depends on the geometry of the probe.

Each digital value received by microprocessor 50 corresponds to different temperatures $T_1$ and $T_2$ sensed by sensors 30 and 34, respectively. The value of k depends on the geometry of the probe 10 and the positioning of sensors 30 and 34, and is determined empirically in a calibration procedure. The calculated value of the surface temperature $T_{surf}$ is an accurate representation of the tissue surface temperature at surface 22. The calculated value of surface temperature takes into account variations in the transducer power level and temperature and variations in the ambient tissue temperature.

The calculated surface temperature can be indicated on a display 54 of the ultrasound imaging instrument as a numerical temperature value. Alternatively, or in addition to the numerical indication of surface temperature, the calculated surface temperature can be compared by microprocessor 50 with a temperature limit. When the surface temperature exceeds a predetermined temperature limit, typically 41° C., or exceeds a predetermined increase above the ambient tissue temperature, a warning can be given on display 54. In addition, or as an alternative to the warning, a control signal can be provided to control the power level supplied to ultrasound transducer 12.

Referring to FIG. 2, a power source 58 supplies electrical energy, typically at a frequency in the range of 1 MHz to 10 MHz, to ultrasound transducer 12. A control signal from microprocessor 50 can reduce the power level supplied by source 58 or can deenergize the power source 58 entirely when the calculated surface temperature exceeds the temperature limit.

Thus, the microprocessor 50 receives and stores the digital values which represent the temperatures sensed by sensors 30 and 34. The tissue surface temperature $T_{surf}$ is calculated in accordance with Equation (1). The calculated surface temperature can be forwarded by the microprocessor 50 to the display 54. If desired, the calculated surface temperature is compared with a temperature limit as described above, and a warning signal is sent to the display 54 when the temperature limit is exceeded. Similarly, a control signal can be sent to the power source 58 when the calculated surface temperature exceeds a temperature limit. The surface temperature is typically calculated at a rate of two times per second.

The invention has been described thus far in connection with an ultrasound imaging probe designed for internal use. It will be understood that the temperature measurement technique is not limited to ultrasound imaging and is not limited to internal use. In general, the temperature measurement technique described above can be used to measure the surface temperature of biological tissue adjacent to any transducer that applies energy to the tissue.

Figure 3:
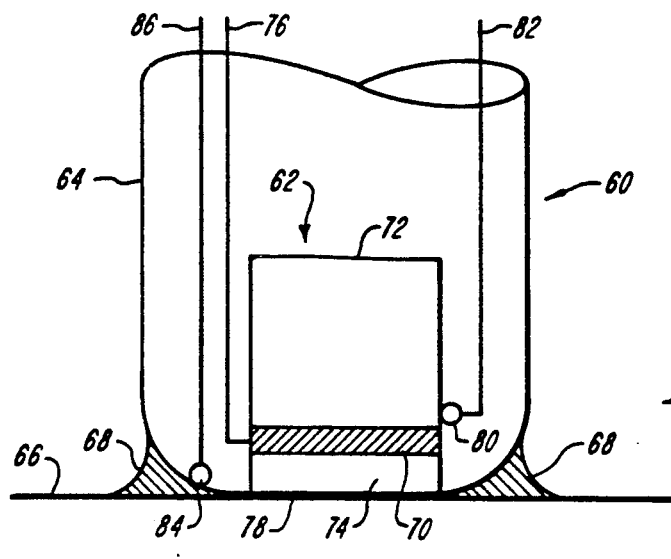
FIG. 3 is a simplified schematic diagram of an ultrasound imaging device for surface use.

An ultrasound imaging device 60 for surface use is shown schematically in FIG. 3. An ultrasound transducer 62 is mounted within a housing 64. The housing 64 is fabricated of a biologically compatible material and is acoustically coupled to tissue 66 of a patient's body with acoustic coupling gel 68. The ultrasound transducer 62 includes a piezoelectric crystal 70 mounted on a backing material 72. An ultrasound lens 74 fabricated of an electrically insulating material is mounted between the piezoelectric crystal 70 and an external surface 78 of the housing 64. The piezoelectric crystal 70 is connected by electrical leads 76 to power source 58 (FIG. 2). The ultrasound transducer 62 transmits ultrasound energy through the surface 78 of device 60 into the adjacent tissue 66.

A first temperature sensor 80 mounted in thermal proximity to piezoelectric crystal 70 for measurement of a temperature that is proportional to the temperature of the emitting face of ultrasound transducer 62. The temperature sensor 80 is connected by electrical leads 82 to processing circuitry as shown in FIG. 2 and described above. A second temperature sensor 84 is mounted in housing 64 for measurement of the ambient body temperature of the patient. The temperature sensor 84 is connected by electrical leads 86 to the processing circuitry. Temperature sensor 84 is positioned in device 60 as far as is practical from ultrasound transducer 62 in a position to measure the ambient tissue temperature of the patient. The surface temperature of the tissue at surface 78 is calculated from the temperatures sensed by temperature sensors 80 and 84 as described above in connection with FIG. 2.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for determining the surface temperature of tissue adjacent to a transducer that applies energy to the tissue, comprising the steps of:
   measuring a first temperature representative of the temperature of the transducer;
   measuring a second temperature representative of the ambient temperature of the tissue in a region that is thermally isolated from the transducer; and
   calculating the surface temperature of the tissue adjacent to the transducer from the first measured temperature and the second measured temperature.

2. A method as defined in claim 1 wherein said transducer comprises an ultrasound transducer and wherein the step of measuring the first temperature is performed with a first temperature sensor in thermal proximity to said ultrasound transducer.

3. A method as defined in claim 2 wherein said transducer is mounted in a probe and wherein the step of measuring the second temperature is performed with a second temperature sensor attached to said probe and thermally isolated from the transducer.

4. A method as defined in claim 1 wherein the step of calculating the surface temperature is performed in accordance with:

$$T_{surf} = (1 - 1/k)T_2 + (1/k)T_1$$

where:
- $T_{surf}$ = surface temperature;
- $T_1$ = first temperature;

$T_2$ = second temperature; and
$k$ = a constant.

5. A method as defined in claim 1 further including the step of reducing the power applied to said transducer when said calculated surface temperature exceeds a temperature limit.

6. A method for determining and controlling the surface temperature of tissue adjacent to a transducer that applies energy to the tissue, comprising the steps of:
   measuring a first temperature representative of the temperature of the transducer;
   measuring a second temperature representative of the ambient temperature of the tissue in a region that is isolated from the transducer; and
   calculating the surface temperature of the tissue adjacent to the transducer from the first measured temperature and the second measured temperature; and
   controlling the energy applied to said transducer in response to said calculated surface temperature.

7. Apparatus for determining the surface temperature of tissue adjacent to a transducer that applies energy to the tissue, comprising:
   means for measuring a first temperature representative of the temperature of the transducer;
   means for measuring a second temperature representative of the ambient temperature of the tissue in a region that is thermally isolated from the transducer; and
   means for calculating the surface temperature of the tissue adjacent to the transducer from the first measured temperature and the second measured temperature.

8. Apparatus as defined in claim 7 wherein said means for measuring a first temperature comprises a first temperature sensor in thermal proximity to said transducer.

9. Apparatus as defined in claim 8 wherein said transducer is mounted in a probe and wherein said means for measuring a second temperature comprises a second temperature sensor attached to said probe and thermally isolated from said transducer.

10. Apparatus as defined in claim 9 wherein said transducer comprises a piezoelectric crystal for transmitting ultrasound energy.

11. Apparatus for application of ultrasound energy to biological tissue, comprising:
    a probe having an ultrasound transducer mounted therein;
    a first temperature sensor mounted in said probe for sensing a first temperature representative of the temperature of an emitting face of said ultrasound transducer;
    a second temperature sensor mounted in said probe for sensing a second temperature representative of the ambient temperature of the biological tissue in a region that is thermally isolated from the ultrasound transducer;
    a power source for energizing said ultrasound transducer; and
    means for calculating the surface temperature of the tissue adjacent to the ultrasound transducer from the first sensed temperature and the second sensed temperature 12. Apparatus as defined in claim 11 further including means for controlling said power source in response to said calculated surface temperature.

13. Apparatus as defined in claim 12 wherein said second temperature sensor is in thermal contact with said biological tissue during application of ultrasound energy to said biological tissue.

14. Apparatus as defined in claim 11 further including means for controlling said power source such that the ultrasound energy applied by said ultrasound transducer is reduced when said calculated surface temperature exceeds a temperature limit.

15. Apparatus as defined in claim 11 wherein said first temperature sensor is in thermal proximity to said ultrasound transducer.

16. Apparatus as defined in claim 15 wherein said ultrasound transducer comprises a piezoelectric crystal attached to a backing material and wherein said first temperature sensor is attached to said backing material.

17. A method for controlling the surface temperature of tissue adjacent to an ultrasound transducer that applies ultrasound energy to the tissue, comprising the steps of:
    measuring a first temperature representative of the temperature of the ultrasound transducer;
    measuring a second temperature representative of the ambient temperature of the tissue in a region that is thermally isolated from the ultrasound transducer;
    calculating the surface temperature of the tissue adjacent to the ultrasound transducer from the first measured temperature and the second measured temperature; and
    reducing the ultrasound energy transmitted by said ultrasound transducer when said calculated surface temperature exceeds a temperature limit.

18. A method as defined in claim 17 wherein the step of calculating the surface temperature is performed in accordance with:

$$T_{surf} = (1 - 1/k)T_2 + (1/k)T_1$$

where:
$T_{surf}$ = surface temperature;
$T_1$ = first temperature;
$T_2$ = second temperature; and
$k$ = a constant.

* * * * *